(12) United States Patent
Itou et al.

(10) Patent No.: US 7,091,043 B2
(45) Date of Patent: Aug. 15, 2006

(54) METHOD FOR MEASURING WATER CONCENTRATION IN AMMONIA

(75) Inventors: Taizou Itou, Kanagawa (JP); Hideki Hayashida, Kanagawa (JP); Yasuhiro Kosuge, Kanagawa (JP); Fumiyasu Ishigaki, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 25 days.

(21) Appl. No.: 09/732,712

(22) Filed: Dec. 11, 2000

(65) Prior Publication Data

US 2002/0061594 A1    May 23, 2002

Related U.S. Application Data

(60) Provisional application No. 60/176,799, filed on Jan. 19, 2000.

(30) Foreign Application Priority Data

Dec. 10, 1999  (JP) ............... 11-351585
Nov. 14, 2000  (JP) ............... 2000-346044

(51) Int. Cl.
*G01N 33/00* (2006.01)

(52) U.S. Cl. ............ 436/113; 436/164; 436/52; 436/39

(58) Field of Classification Search ............ 436/39, 436/52, 113, 164
See application file for complete search history.

(56) References Cited

U.S. PATENT DOCUMENTS 4,023,193 A * 5/1977 Schroter et al. ............ 396/564
4,075,306 A * 2/1978 Muromura ............ 423/352
5,846,386 A  12/1998 Hoffman et al.
6,040,915 A  3/2000 Wu et al.

FOREIGN PATENT DOCUMENTS

| JP | 61-095229 A | 5/1986 |
| JP | 05-157689 A | 6/1993 |
| JP | 08-008185 A | 1/1996 |
| JP | 8-201370    | 9/1996 |
| JP | 9-142833    | 6/1997 |

(Continued)

OTHER PUBLICATIONS

Wu et al. "Quantitative Analysis of Trace Moisture in NH3 Gas with Dual-Cell Near-Infrared Diode Laser Absorption Spectroscopy", Anal. Chem., 1998, v. 70, pp. 3315-3321.*

(Continued)

*Primary Examiner*—Yelena G. Gakh
(74) *Attorney, Agent, or Firm*—Sughrue Mion, PLLC

(57) ABSTRACT

Method and apparatus for measuring a water concentration in ammonia, comprising using ammonia having a water concentration of 10 ppm or less as a reference gas, introducing the ammonia at a constant flow rate into a multi-reflection long optical path gas cell, and measuring infrared absorption intensity of water at at least one measurement wave number in the range of from 3,500 to 4,000 cm$^{-1}$, from 2,600 to 3,100 cm$^{-1}$, or from 1,900 to 2,400 cm$^{-1}$ at which infrared absorptions of ammonia and water do not overlap.

According to the present invention, analysis of water in a low concentration range of 10 ppm or less in ammonia gas and liquefied ammonia can be performed in a simple and convenient manner.

12 Claims, 4 Drawing Sheets

FOREIGN PATENT DOCUMENTS

| | | |
|---|---|---|
| JP | 09-142833 A | 6/1997 |
| JP | 10-281988 A | 10/1998 |
| JP | 11-507004 A | 6/1999 |
| JP | 11-509980 A | 6/1999 |
| WO | WO 96/39263 A1 | 12/1996 |
| WO | WO 96/39264 A1 | 12/1996 |
| WO | WO 96/39265 A1 | 12/1996 |

OTHER PUBLICATIONS

Wu et al. "Absorption Spectrometry of Trace Moisture in Ammonia Gas with a 1371 nm Distributed-Feedback Diode Laser", Jap. J. Appl. Phys., 1999, 38(8), 4788-4793.*

Girard et al. "PPB-Level Hydrometry in Nitrogen and ESG's Using Tunable Diode Laser Spectroscopy", The International Symposium on Semiconductor Manufacturing, Oct. 1996, pp. 325-328.*

"The International Association for the Properties of Water and Steam" Gaithersburg, MD Sep. 2001.*

Guillevic et al. Vapor-liquid equilibrium data for the binary system water-ammonia at 403.1 K, 453.1 K, 503.1 K up to 7.0 MPa J. Chem. Eng. Data, 30, 332 (1985).*

Kästle et al. "Using Diode Laser Spectroscopy to Monitor Process Gas Purity", Microcontamination, Nov. 1991, pp. 27-31.*

Wu Shang-Qian et al, "Absorption Spectrometry of Trace Moisture in Ammonia Gas with a 1371 nm Distributed-Feedback Diode Laser" *Japanese Journal of Applied Physics*, vol. 38, No. 8, pp. 1478-4793, Aug. 1999, XP002139960.

Communications from European Patent Office.

* cited by examiner

Table Contents Here

METHOD FOR MEASURING WATER CONCENTRATION IN AMMONIA

CROSS-REFERENCE TO RELATED APPLICATION

This application is based on the provisions of 35 U.S.C. § 111(a) with claiming the benefit of filing date of U.S. provisional application Ser. No. 60/176,799 filed on Jan. 19, 2000 under the provisions of 35 U.S.C. § 111(b), pursuant to 35 U.S.C. § 119(e)(1).

TECHNICAL FIELD

The present invention relates to a method for measuring a water concentration in ammonia. More specifically, the present invention relates to a method for measuring a water concentration in ammonia using infrared spectrometry, particularly, a concentration of trace water contained in high-purity ammonia used as a raw material in the production of a semiconductor, for example, a GaN-type compound semiconductor, and to an infrared measuring apparatus using the method, to a method for producing ammonia having a decreased water content, to ammonia having a decreased water content, and to a semiconductor nitride film and group III–V compound semiconductor produced using the ammonia.

BACKGROUND ART

It is known that the water content of a raw material gas used in the production of a semiconductor greatly affects the device characteristics. In particular, for the production of a GaN crystal, which is one of the blue light emitting devices, ammonia having a low water concentration is necessary. In order to measure the water concentration in ammonia, various methods have heretofore been proposed. Particularly for measuring water content in a low concentration in ammonia, (1) gas chromatography (GC method), (2) thermal decomposition dew point method, (3) laser spectrometry and (4) infrared spectrometry are known.

JP-A-9-142833 (the term JP-A as used herein means "unexamined published Japanese patent application") discloses a method of reacting water in ammonia with calcium carbide as a reacting agent and detecting the acetylene generated by GC method. This method has a problem in that not only the water content but also organic impurities in the calcium carbide reacted are detected and to avoid this, high-purity and stabilized calcium carbide is necessary but this is hardly available at present. In addition, the GC method is low in the accuracy and not practical for the analysis in the level of several ppm or less because the system has a switch cock for feeding a sample or a backflash cock for removing ammonia before it enters the detector, and the water adsorption onto the inner surface of pipelines increases.

SEMI Standard (SEMI C3.12-94) and JP-A-8-201370 describe a thermal decomposition dew point method. The thermal decomposition dew point method is a method of decomposing ammonia into nitrogen and hydrogen at a high temperature near 1,000° C. using a Ni catalyst or a noble metal catalyst, and measuring the water content by a dew-point instrument. According to this method, oxygen in the gas reacts with hydrogen to produce water and the water content could be determined in excessive values. Oxygen is contained not only in the raw material gas but also as an oxide of the catalyst or pipeline material exposed to high temperatures, which may also cause hydrogen reduction to produce water. Therefore, the reliability for accuracy decreases in the measurement of water content of 1 ppm or less. Moreover, use of flammable ammonia in a high temperature environment of 1,000° C. or more is dangerous and safety equipment in a large scale is necessary. Thus, this method is not simple and convenient.

Laser spectrometry is described in *Proceedings of the 5th International Symposium on Semiconductor Manufacturing* (1996. jointly sponsored by UCS/IEEE/SEMI), page 321. In measuring the water absorption in the near infrared region by laser spectrometry, since water is present in the vicinity of ammonia in the absorption region, a wavelength resolving power of high level is necessary. However, at present the separation cannot be attained due to the interaction between gas molecules. Therefore, ammonia gas having a decreased water content as low as negligible must be used as a reference gas. However, it has been heretofore difficult to simply and conveniently prepare high-purity ammonia which has a decreased water content and can be used as the reference gas.

The infrared spectrometry has a problem in that the ammonia has a broad absorption band and particularly when a water concentration of 100 ppm or less is measured, the absorptions by ammonia and the absorptions by water cannot be easily separated even if the former are weak because such an absorption by ammonia is present near the absorption by water in many cases. Furthermore, similarly to the above-described laser spectrometry, ammonia gas having a decreased water content as low as negligible must be used as a reference gas but this has been heretofore difficult to obtain.

As described above, conventionally known methods for measuring a water concentration in ammonia have various problems particularly in the case of measuring the water content in a low concentration in ammonia. Thus, more improvements are being demanded.

DISCLOSURE OF THE INVENTION

The present invention has been made under these circumstances and the objects of the present invention are to provide a method for measuring a water concentration in ammonia, in particular a method for measuring a water concentration in ammonia using infrared spectrometry, which can measure the water content particularly in a low concentration in ammonia, and to provide an infrared measuring apparatus using the method, a method for producing ammonia having a decreased water content, ammonia having a decreased water content, and a semiconductor nitride film and group III–V compound semiconductor produced using the ammonia.

Means to Solve the Problems

As a result of extensive investigations to attain these objects, the present inventors have found that in the method of measuring a water concentration in ammonia using infrared spectrometry, the gaseous phase moiety of liquefied ammonia having a water concentration of 10 ppm or less can be used as a reference gas because the water content is very small. Furthermore, the present inventors have found that the above-described objects can be attained by using a method of introducing an ammonia gas into a multi-reflection long optical path cell at a constant flow rate and measuring it at a wave number having no overlapping between the infrared absorption by ammonia and the infrared absorption by water, in combination with an infrared measuring apparatus equipped with a vaporizer for vaporizing the liquefied ammonia and a flow rate-controlling unit. The present invention has been accomplished based on these findings.

That is, the present invention relates to a method for measuring a water concentration in ammonia using infrared spectrometry, an infrared measuring apparatus, a method for producing ammonia having a decreased water content, ammonia having a decreased water content, and a semiconductor nitride film and group III–V compound semiconductor produced using the ammonia as described in 1 to 21 below:

1. A method for measuring a water concentration in liquefied ammonia having a water concentration of no more than 10 ppm, comprising introducing a gaseous phase moiety of liquefied ammonia, said liquefied ammonia having a water concentration of 10 ppm or less, as a reference gas into a multi-reflection long optical path cell, measuring infrared (IR) spectrum of the reference gas as a background of an IR spectrometer, introducing a gas obtained by vaporizing liquefied ammonia as a sample at a constant flow rate into the cell, measuring infrared (IR) spectrum of the sample employing the background of the spectrometer, measuring absorption intensity in the IR spectrum of the sample at an infrared wave number at which water absorbs IR and at which infrared absorptions of water and ammonia do not overlap, and determining the water concentration based on the measured absorption intensity from a water concentration calibration curve prepared in advance.
2. The method for measuring a water concentration in ammonia as described 1 above, wherein the measurement wave number used is in the range of from 3,500 to 4,000 $cm^{-1}$, from 2,600 to 3,100 $cm^{-1}$, or from 1,900 to 2,400 $cm^{-1}$.
3. The method for measuring a water concentration in ammonia as described in 2 above, wherein the measurement wave number is in the range of from 3,500 to 4,000 $cm^{-1}$ (variation width: ±1 $cm^{-1}$).
4. The method for measuring a water concentration in ammonia as described in 3 above, wherein the measurement wave number is one or more selected from the group consisting of 3801, 3807, 3816, 3821, 3837 and 3854 $cm^{-}$ (variation width ±1 $cm^{-1}$).
5. The method for measuring a water concentration in ammonia as described in any one of 1 to 3 above, wherein the ammonia is obtained by vaporizing liquefied ammonia.
6. The method for measuring a water concentration in liquefied ammonia as described in 1 above, wherein the liquefied ammonia has a water concentration of 10 ppm or less.
7. The method for measuring a water concentration in liquefied ammonia as described in 6 above, wherein the liquefied ammonia that is to be measured has a water concentration of 1 ppm or less and the liquefied ammonia that is employed to obtain a gaseous phase moiety as a reference gas has a water concentration of 1 ppm or less.
8. The method for measuring a water concentration in liquefied ammonia as described in 7 above, wherein the liquefied ammonia that is to be measured has a water concentration of 0.1 ppm or less and the liquefied ammonia that is employed to obtain a gaseous phase moiety as a reference gas has a water concentration of 0.1 ppm or less.
9. The method for measuring a water concentration in ammonia as described in 1 above, wherein ammonia gas is introduced into the multi-reflection long optical path gas cell at a flow rate of from 0.1 to 5 L/min.
10. The method for measuring a water concentration in ammonia as described in 1 above, wherein an infrared ray is multi-reflected to have an infrared optical path length of from 1 to 40 m.
11. An infrared measuring apparatus comprising an infrared spectroscope, a long optical path gas cell, a flow rate controlling unit and a vaporizer, wherein ammonia gas vaporized by the vaporizer is fed into the flow rate controlling unit, the ammonia gas is introduced from the flow rate controlling unit into the long optical path gas cell at a constant flow rate, and the water content of ammonia in the long optical path gas cell is measured by the infrared spectroscope.
12. The infrared measuring apparatus as described in 11 above, wherein the long optical path gas cell has a volume of from 0.1 to 5 L.
13. A method for producing ammonia having a decreased water content, wherein the method comprises the steps of distilling crude ammonia and measuring a water concentration in ammonia using a measurement method as described in any one of 1 to 10 above.
14. A method for producing ammonia having a decreased water content, wherein the method comprises the steps of purifying crude ammonia by contacting it with at least one purifying agent selected from the group consisting of metals, metal oxides and zeolite and measuring a water concentration in ammonia using a measurement method as described in any one of 1 to 10 above.
15. The method for producing ammonia as described in 13 or 14 above, wherein ammonia having a water content of 1 ppm or less is produced.
16. The method for producing ammonia as described in 15 above, wherein ammonia having a water content of 0.1 ppm or less is produced.
17. Ammonia having a water content decreased to 1 ppm or less produced by a method as described in 15 above.
18. Ammonia having a water content decreased to 0.1 ppm or less produced by a method as described in 16 above.
19. A semiconductor nitride film produced using ammonia having a decreased water content obtained by a method as described in any one of 13 to 16 above.
20. A group III–V compound semiconductor produced using ammonia having a decreased water content obtained by a method as described in any one of 13 to 16 above.
21. The group III–V compound semiconductor as described in 20 above, wherein the group III–V compound semiconductor is GaN, $In_xGa_{1-x}N$, $B_xGa_{1-x}N$, $Al_xGa_{1-x}N$, $In_xAl_yGa_{1-x-y}N$, $GaN_pAs_{1-p}$, $GaN_pAs_qP_{1-p-q}$, or $In_xGa_{1-x}N_pAs_{1-p}$ (provided that x, y, p, and q are numbers that satisfy 0<x, y, p, q<1).

MODE FOR CARRYING OUT THE INVENTION

Figure 1:
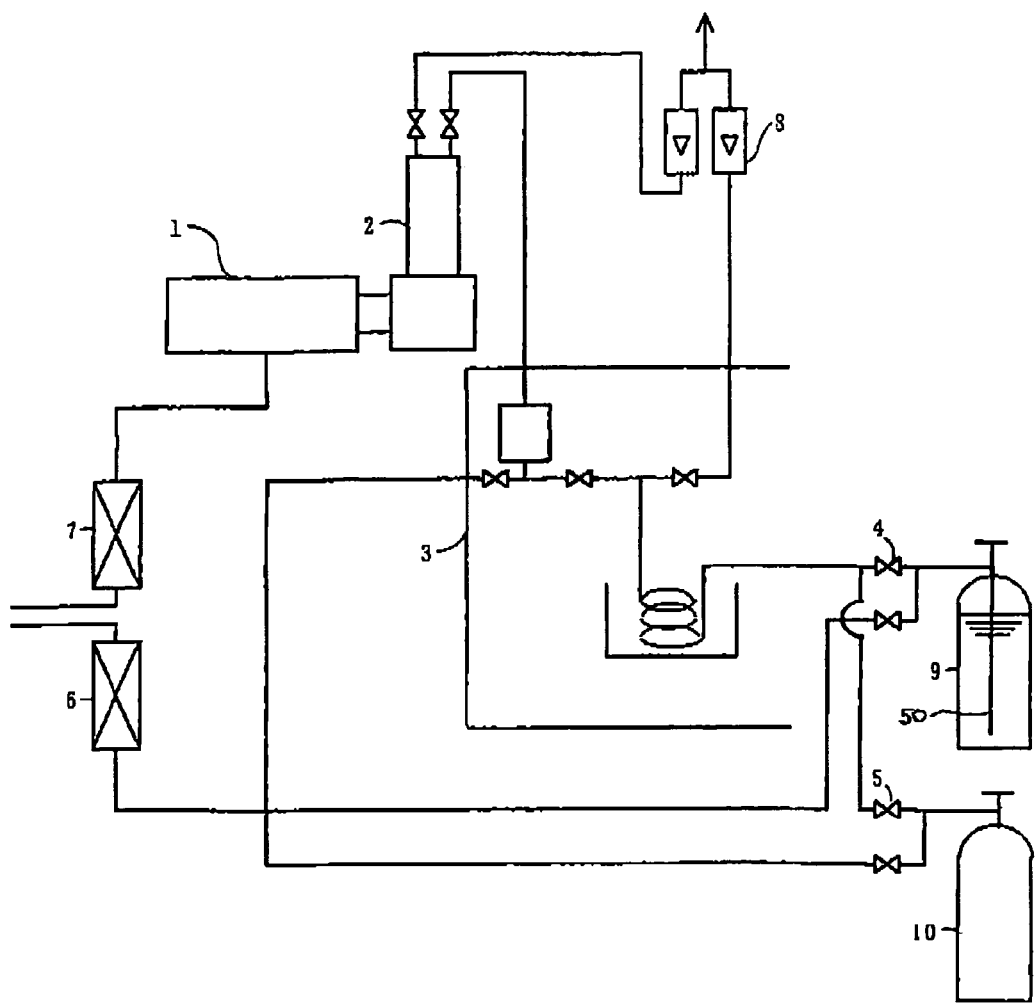
FIG. 1 is a view showing an apparatus for infrared spectrometry for measuring a water concentration in ammonia according to the present invention.

The present invention provides "a method for measuring a water concentration in ammonia, where the gaseous phase moiety of liquefied ammonia having a water concentration of 10 ppm or less is used as a reference gas, ammonia is introduced into a multi-reflection long optical path cell at a constant flow rate and the infrared absorption intensity is measured at a wave number having no overlapping of the infrared absorption by ammonia and the infrared absorption by water," and also provides "an infrared measuring apparatus capable of measuring the water content in both ammonia gas and liquefied ammonia, which is equipped with a vaporizer halving a function of controlling the temperature and a flow rate controlling unit for introducing a gas into a gas cell at a constant flow rate," "a method for producing ammonia having a decreased water content, comprising the steps of purifying crude ammonia and measuring a water concentration in the ammonia using the above-described measurement method," "ammonia having a decreased water content as low as 1 ppm or less obtained by the above method," and "a semiconductor nitride film and group III–V compound semiconductor produced using the above-described ammonia having a decreased water content."

As described above, in the case of measuring the water content in ammonia by infrared spectrometry ammonia gas having water content as small as negligible needs be used as a reference gas. To this purpose, the present inventors have measured the gas-liquid partition coefficient of water distributed to the gaseous phase and the liquid phase of liquefied ammonia and as a result, this was revealed to be a very small value with gaseous phase concentration/liquid phase concentration being from 0.01 to 0.1. Heretofore, no paper has reported on the gas-liquid partition coefficient of liquefied ammonia in a water concentration region of 10 ppm or less. However, from the result above, it has been found that the gaseous phase of ammonia having a very low liquid phase water concentration is ammonia gas having a decreased water content as low as negligible and can be used as the reference gas in the infrared spectrometry of the present invention.

At this time the calibration curve used for the determination of a water concentration is obtained by mixing 50% of the above described ammonia gas having a very low water concentration and 50% of nitrogen having a water concentration of from 0.5 to 2 ppm and determining the correlation between the water concentration and the infrared absorption intensity at a measurement wave number selected from the ranges of from 3,500 to 4,000 $cm^{-1}$, from 2,600 to 3,100 $cm^{-1}$, and from 1,900 to 2,400 $cm^{-1}$. For simply determining the water concentration of ammonia gas, it may also be possible to correct and convert a value obtained from a water concentration calibration curve of nitrogen 100% gas.

When the infrared absorption wave number of ammonia and the infrared absorption wave number of water are examined in particular, the infrared absorption wave numbers of water present in the ranges of from 3,500 to 4,000 $cm^{-1}$, from 2,600 to 3,100 $cm^{-1}$ and from 1,900 to 2,400 $cm^{-1}$ are found to be small in the influence of ammonia and free of overlapping with the infrared absorption by ammonia. Therefore, the infrared absorption intensity is measured using one or more of wave numbers falling within these ranges, preferably one or more wave number selected froni the group consisting of 3801, 3807, 3816, 3821, 3837 and 3854$cm^{-1}$ (variation width: ±1cm).

Ammonia gas is introduced into a multiple reflection long optical path cell and determined on the infrared absorption intensity. The infrared measuring apparatus of the present invention has a vaporization unit so that it can analyze even liquefied ammonia and can be suitably used for the measurement of a trace water concentration of 10 ppm or less in ammonia. At the time of introducing ammonia gas into the multiple reflection long optical path cell, the flow rate of ammonia gas is controlled using a flow rate controlling unit. The flow rate is constant and is suitably from 0.1 to 5 L/min, preferably from 0.5 to 3 L/min. If the flow rate is less than 0.1 L/min. reproducibility of the measurement results cannot be obtained. Whereas if the flow rate exceeds 5 L/min, the ammonia gas disadvantageously contaminates the measurement environment. The infrared ray is multi-reflected so as to increase the sensitivity, and the optical path length here is suitably from 1 to 40 m, preferably from 2 to 30 m, more preferably from 4 to 20 m. With this optical path length, the sensitivity is remarkably improved and good sensitivity can be obtained.

The method for measuring a water concentration in ammonia and the infrared measuring apparatus of the present invention are described below by referring to a schematic view of the apparatus shown in FIG. 1.

The apparatus shown in FIG. 1 is an apparatus for infrared spectrometry, equipped with an infrared spectroscope 1 for measuring water absorption intensity, a long optical path gas cell 2 for introducing ammonia gas, a vaporization unit 3 for vaporizing liquefied ammonia, a connecting line 4 for connecting a measurement sample cylinder 9, a connecting line 5 for connecting a reference gas cylinder 10, a water adsorption barrel 6 for drying nitrogen used for purging the pipelines, a water adsorption barrel 7 for drying nitrogen used for purging the infrared spectroscope, and a flow meter 8.

Figure 3:
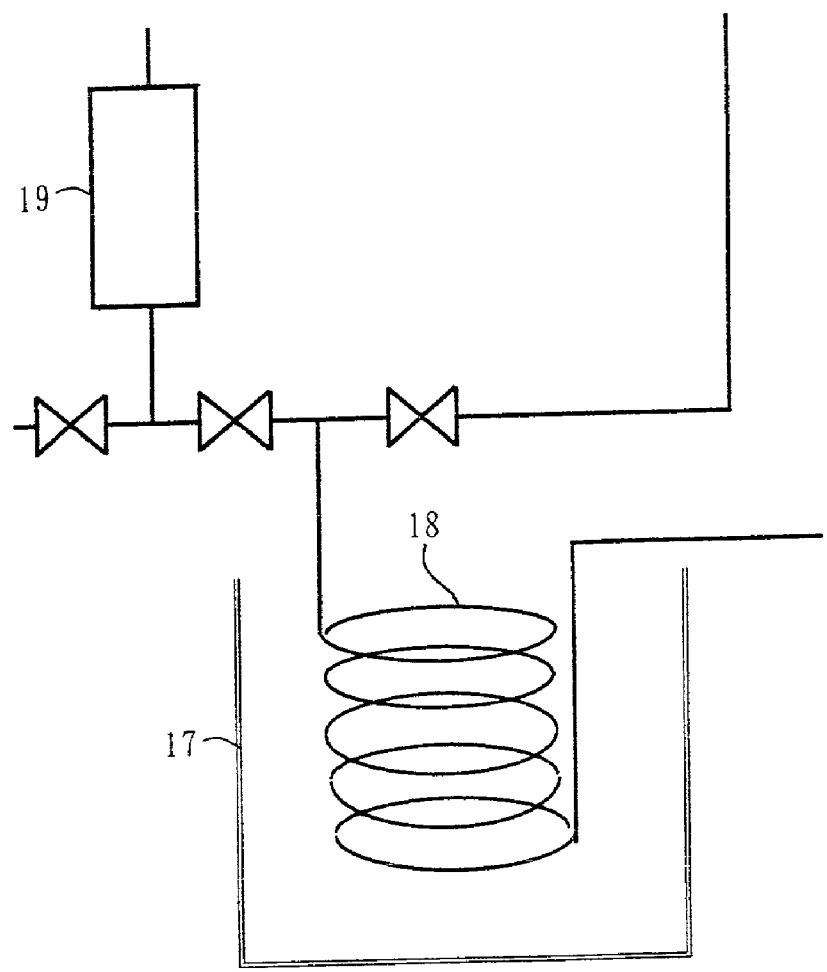
FIG. 3 is an enlarged view showing the vaporization unit shown in FIG. 1.

For measuring the water content in ammonia, the measurement sample cylinder 9 and the reference gas cylinder 10 are connected to the connecting line 4 and the connecting line 5, respectively. Dry nitrogen passed through the adsorption barrel 6 is allowed to flow through the connecting lines 4 and 5, a flow rate controlling unit 19 shown in FIG. 3 is adjusted to give a constant flow rate in the flow meter 8, and the pipelines are dried for 30 minutes or more.

Figure 2:
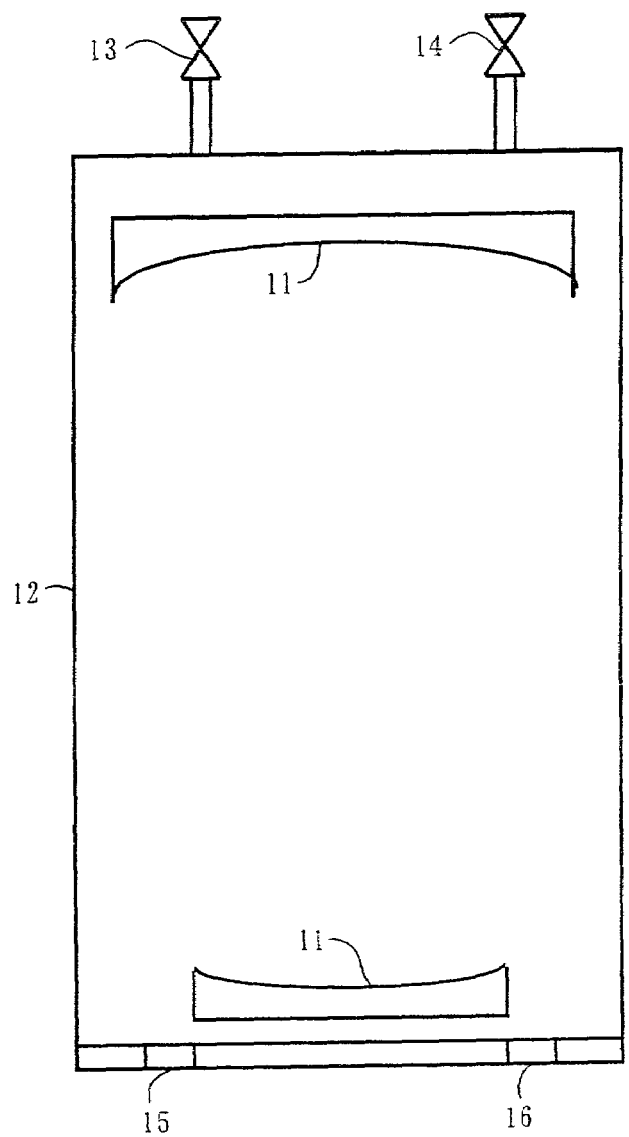
FIG. 2 is an enlarged cross sectional view of the long optical path cell shown in FIG. 1.

Subsequently dry nitrogen is introduced into the long optical path gas cell 2. FIG. 2 is an enlarged cross sectional view of a long optical path cell part. In FIG. 2, reference numeral 11 denotes an infrared ray reflection mirror, 12 denotes an acuminous barrel, 13 denotes a gas inlet valve, 14 denotes a gas outlet valve, 15 is an infrared ray entering window, and 16 denotes an infrared exiting window. The inside of the gas cell 2 is dried to decrease the water content in nitrogen introduced in the gas cell 2 to 1 ppm or less. Thereafter, feeding of dry nitrogen is stopped and then ammonia gas is introduced from the reference gas cylinder into the gas cell 2. At this time, similarly to nitrogen, the flow rate is controlled to a constant flow rate by the flow rate-controlling unit 19. The reference gas is passed for 60 minutes or more and after replacing the gas in the gas cell 2, the infrared absorption spectrum is measured. The results obtained are used as the background of the infrared spectroscope 1.

Then, passing of the reference gas is stopped and ammonia gas or liquefied ammonia is allowed to flow from the measurement sample cylinder 9 connected to the connecting line 4. In the case of ammonia gas, the gas flow rate is controlled to a constant flow rate by the flow rate-controlling unit 19. In the case of liquefied ammonia, a thermostatic chamber 17 is set at a temperature of from 40 to 150° C. and after the liquefied ammonia flowing through the heated vaporizer 18 is vaporized, the gas is controlled to a constant flow rate. In either case, the gas is passed through the gas cell at the same flow rate as in the measurement of the reference gas for 60 minutes or more and after replacing the gas within the gas cell 2, the water absorption intensity is measured.

The measurement sample gas container 9 may have any structure as far as liquefied ammonia can be taken out from the container. Such structures are well known in the art. FIG. 1 illustrates an example of such a well known structure. FIG. 1 illustrates the inside of the container 9. In FIG. 1, the dipping tube 50 of the container 9 enables liquefied ammonia to be withdrawn from the interior of the container.

FIG. 3 shows a vaporization unit 3 which is used in the case of measuring the water content of liquefied ammonia. Liquefied ammonia is introduced into the SUS made vaporizer 18 (diameter: ¼" to ¹⁄₁₆", length: 0.5 to 5 m) heated at from 40 to 150° C. using the thermostatic chamber 17 and after the gasification by heating, the flow rate is controlled by the flow rate controlling unit 19. The gas flow rate is suitably from 0.1 to 5 L/min.

Figure 4:
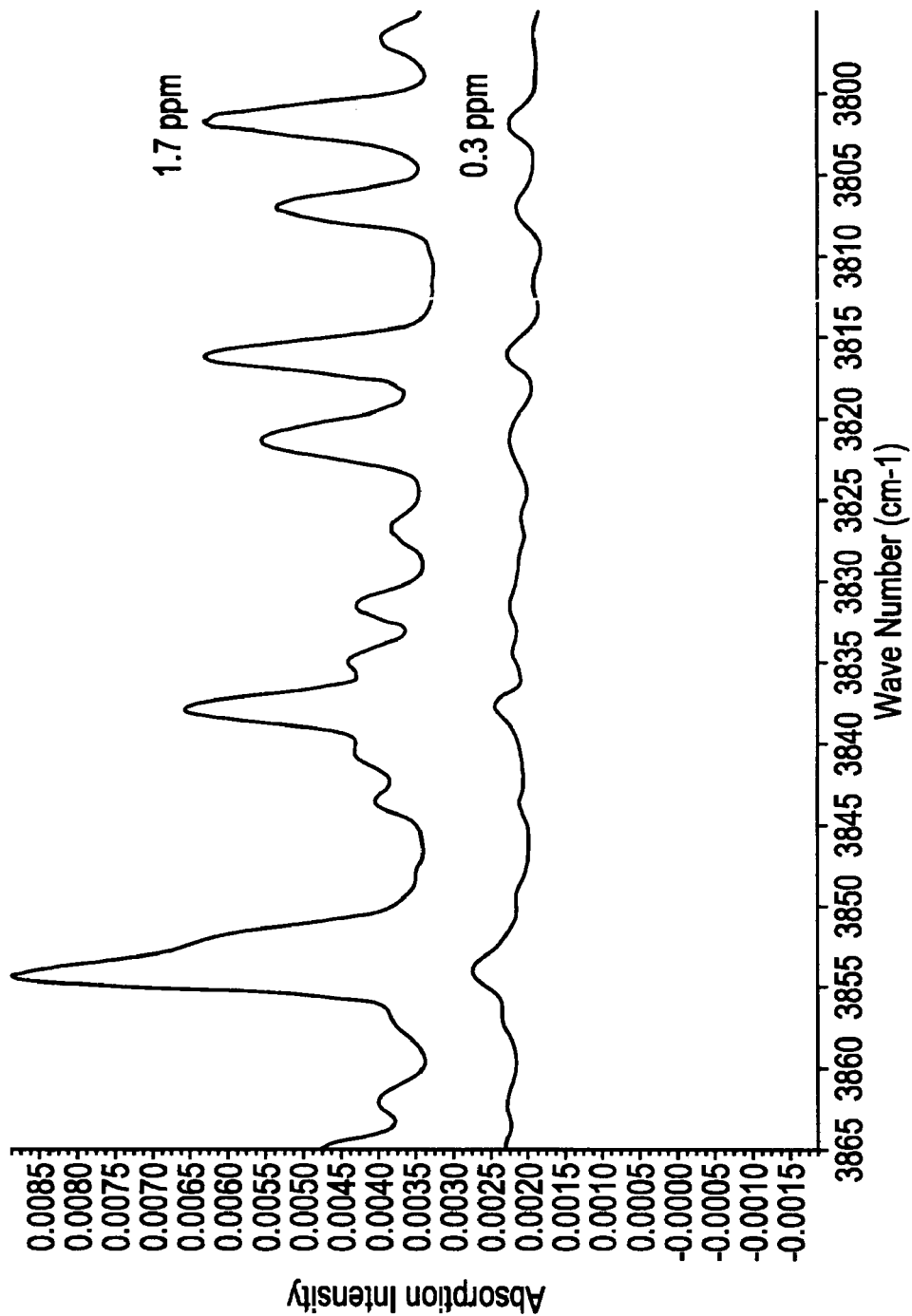
FIG. 4 is a diagram showing infrared absorption spectra of water in ammonia measured by the method of the present invention.

FIG. 4 shows the results obtained when two kinds of liquefied ammonia different in the water concentration (1.7 ppm or 0.3 ppm) each is vaporized using the vaporization unit 3 with the background of the reference gas and the ammonia gas is introduced into a gas cell having an optical path length of 10 m at a flow rate of 2 L/min and analyzed. From the results obtained, it is seen that the wave number used in the measurement is preferably $3801 \pm 1$ cm$^{-1}$, $3807 \pm 1$ cm$^{-1}$, $3816 \pm 1$ cm$^{-1}$, $3821 \pm 1$ cm$^{-1}$, $3837 \pm 1$ cm$^{-1}$ or $3854 \pm 1$ cm$^{-1}$.

Next, the method for producing ammonia having a decreased water content will be described below.

The method for producing ammonia having a decreased water content according to the present invention comprises the steps of purifying crude ammonia and measuring a water concentration using the above-described measurement method. The water content of ammonia produced using the method for producing ammonia having a decreased water content according to the present invention is 1 ppm or less, preferably 0.1 ppm or less.

As the crude ammonia provided in the purifying step, any ammonia produced by conventional industrial production methods may be used and the water content thereof is not particularly limited and preferably 100 to 1,000 ppm. The method which is used in the step of purifying ammonia may be a method which uses, for example, distillation. The distillation method may be either simple distillation or rectification as far as the water content can be decreased sufficiently. The method may be either a batch process or a continuous process.

Further, as the method used in the step of purifying ammonia, a method in which crude ammonia is contacted with a purifying agent, e.g., a metal such as zirconium, barium, or calcium or oxides thereof, alloy of iron and manganese, zeolite, etc. may be used. These purifying agents may be used alone or two or more of them may be used as mixtures in any desired proportions to remove water in ammonia by reaction or adsorption to thereby purify the ammonia. The method in which ammonia is contacted with a purifying agent is preferably a method in which ammonia is contacted with it in a gaseous phase and purification may be performed using a batch process, continuous process, etc. Any purification method may be used as far as the water content in ammonia can be decreased sufficiently.

Next, semiconductor nitride film of the present invention will be described.

As described above, use of the production method of the present invention enables production of ammonia having a decreased water content and use of ammonia having a water content of 1 ppm or less enables production of a semiconductor nitride film. That is, the ammonia having a decreased water content can be used as a raw material gas serving as nitrogen source for producing a nitride film by chemical vapor deposition method (CVD method). In this case, as the gas for forming a nitride film by reacting with ammonia gas, compounds of silicon, titanium, aluminum, tantalum, tungsten, etc.

Representative methods for producing nitride films include high temperature thermal CVD method, plasma CVD method, and optical CVD method, from which the production method can be selected depending on the purpose for which the resulting nitride films are utilized. For example, silicon nitride films can be produced by the reaction between the ammonia gas and a hydride or halide of silicon by a high temperature thermal CVD method. When the nitride films are formed, use of ammonia having a low content of water can decrease $Si_xN_yH_z$ forms in which H is bonded to Si and N in the form of Si—H and N—H, so that the performance of semiconductors can be increased.

Further, use of the ammonia having a decreased water content as described above enables production of group III–V compound semiconductors as shown in the following examples.

First, a sapphire substrate is contained in a reaction chamber and supported on a supporting portion, the reaction chamber is evacuated, and the sapphire substrate is heated to preferably 400° C. using a heater. Then, organogallium such as trimethylgallium and organoaluminum such as trimethylaluminum contained in the container are introduced together with $H_2$ gas into the reaction chamber through respective inlet conduits. At the same time, the ammonia gas supplied from a filling apparatus is introduced into the reaction chamber through an inlet conduit. The organogallium gas, organoaluminum gas, and ammonia gas are used as raw materials to form a buffer layer consisting of $Al_xGa_{1-x}$ on the surface of the sapphire substrate.

Next, the temperature of the substrate is elevated to about 1,150° C. and a Si compound such as silane is supplied into the reaction chamber through a conduit along with supply of the above organogallium, organoaluminum, and ammonia gases to form an n-type clad layer on the buffer layer. Then, together with the above organogallium, organoaluminum, and ammonia gases, a Zn compound such as dimethylzinc supplied from a container is supplied into the reaction chamber through a conduit to form an active layer on the n-type clad layer. Further, together with the above organogallium, organoaluminum, and ammonia gases, an Mg compound such as biscyclopentadienyl magnesium from a container is supplied into the reaction chamber through a conduit to form a p-type clad layer on the active layer. Thereafter, the epitaxial wafer thus fabricated is taken out from the reaction chamber and electrodes are provided on the n-type and p-type clad layers to obtain a GaN-type compound semiconductor device.

According to a production method presented as an example of the above embodiment, the resulting GaN-type compound semiconductor device is excellent in emission characteristics such as luminance. Therefore, production yield can be improved. The reason why the GaN-type compound semiconductor device fabricated by the above production example is excellent in emission characteristics is believed to be attributable to the fact that the decrease in water content in ammonia to 1 ppm or less, preferably 0.1 ppm or less can keep the amount of oxygen which contaminates the n-type and p-type clad layers and active layer formed from the ammonia as raw material to a low level and as a result can prevent the crystallinity of the layers composed of the GaN-type compound semiconductor from being deteriorated.

To add, although in the above embodiment, methods for forming n-type and p-type clad layers and active layer of $Al_xGa_{1-x}N$ as a main component using the above ammonia as a raw material are exemplified, the present invention is not limited thereto. The above-described ammonia may be used in the production of group III–V compound semiconductors by forming on a substrate layers of group III–V compounds such as those containing Ga, In, Al, or B, as a group IIIB element and N, As, or P as a group VB element, for example, GaN, InGaN, BGaN, AlGaN, InGaAlN, GaNAs, GaNAsP, InGaNAs, etc.

Hereafter, the present invention will be described in more detail by an example. However, the present invention is not limited to the example.

EXAMPLE

Crude ammonia having a water content of 300 ppm was continuously purified by distillation under the following conditions. The water content of the obtained liquid phase ammonia was measured by infrared spectrometry under the following conditions to be 0.1 ppm.

(1) Distillation conditions

| | |
|---|---|
| Amount of introduced crude ammonia: | 21 kg/hr |
| Amount of separated high boiling component: | 3 kg/hr |
| Amount of distilled ammonia: | 18 kg/hr |
| Reflux ratio: | 2 |
| Inner pressure of distillation tower: | 0.64 MPa |

(2) Water content measurement conditions

Measurement apparatus
MAGNA IR560 SPECTROMETRE, manufacture by NICOLET INSTRUMENT Corp.
Measurement wave number
3801 cm$^{-1}$, 3807 cm$^{-1}$, 3816 cm$^{-1}$, 3821 cm$^{-1}$, 3837 cm$^{-1}$, 3854 cm$^{-1}$

| | |
|---|---|
| Ammonia gas flow rate | 2 L/min |
| Optical path length | 10 m |
| Vaporization temperature | 80° C. |
| Reference gas | Gaseous phase of purified ammonia distillate |
| Reference gas flow rate | 2 L/min |

INDUSTRIAL APPLICABILITY

As described in the foregoing pages, according to the method and apparatus for measuring a water concentration in ammonia of the present invention, one or more wave number in the ranges of from 3,500 to 4,000 cm$^{-1}$, from 2,600 to 3,100 cm$^{-1}$ and from 1,900 to 2,400 cm$^{-1}$ is used, so that water in a low concentration region of 10 ppm or less can be simply and easily analyzed not only in ammonia gas but also in liquefied ammonia by controlling the temperature and vaporizing it. Furthermore, removal of water in ammonia or the effect of water concentration on the device characteristics can be estimated, so that productivity in the production process can be elevated. Furthermore, use of ammonia having a decreased water content obtained by the production method of the present invention enables improvement in the performance of semiconductor and production of compound semiconductors with excellent emission properties.

What is claimed is:

1. A method for measuring a water concentration in liquefied ammonia having a water concentration of no more than 10 ppm, comprising:
    introducing a gaseous phase moiety of liquefied ammonia, said liquefied ammonia having a water concentration of 10 ppm or less, as a reference gas into a multi-reflection long optical path cell,
    measuring infrared (IR) spectrum of the reference gas as a background of an IR spectrometer,
    introducing a gas obtained by vaporizing liquefied ammonia as a sample at a constant flow rate into the cell,
    measuring infrared (IR) spectrum of the sample employing the background of the spectrometer,
    measuring absorption intensity in the IR spectrum of the sample at an infrared wave number at which water absorbs IR and at which infrared absorptions of water and ammonia do not overlap, and
    determining the water concentration based on the measured absorption intensity from a water concentration calibration curve prepared in advance.

2. The method for measuring a water concentration in liquefied ammonia as claimed in claim 1, wherein said liquefied ammonia that is employed to obtain a gaseous phase moiety as a reference gas has a water concentration of 1 ppm or less and said liquefied ammonia that is vaporized to obtain a sample has a water concentration of 1 ppm or less.

3. The method for measuring a water concentration in liquefied ammonia as claimed in claim 2, wherein said liquefied ammonia that is employed to obtain a gaseous phase moiety as a reference gas has a water concentration of 0.1 ppm or less and said liuuefled ammonia that is vaporized to obtain a sample has a water concentration of 0.1 ppm or less.

4. The method for measuring a water concentration in liquefied ammonia as claimed in claim 1, wherein ammonia gas is introduced into said multi-reflection long optical path cell at a flow rate of from 0.1 to 5 L/min.

5. The method for measuring a water concentration in liquefied ammonia as claimed in claim 1, wherein an infrared ray is multi-reflected to have an infrared optical path length of from 1 to 40 m.

6. A method for producing ammonia having a decreased water content, wherein the method comprises the steps of distilling crude ammonia and measuring a water concentration in aninionia using a measurement method as claimed in claim 1.

7. A method for producing ammonia having a decreased water content, wherein the method comprises the steps of purifying crude ammonia by contacting it with at least one purifying agent selected from the group consisting of metals, metal oxides and zeolite and measuring a water concentration in ammonia using a measurement method as claimed in claim 1.

8. The method for producing ammonia as claimed in claim 6 or 7, wherein ammonia having a water content of 1 ppm or less is produced.

9. The method for producing ammonia as claimed in claim 8, wherein ammonia having a water content of 0.1 ppm or less is produced.

10. The method for measuring a water concentration in ammonia as claimed in claim 1, wherein the gaseous phase moiety employed as the reference gas has a water concentration that is 0.01 to 0.1 times the water concentration of the liquefied ammonia.

11. The method for measuring a water concentration in ammonia as claimed in claim 1, wherein the measurement wave number used is in the range of from 3,500 to 4,000 $cm^{-1}$, from 2,600 to 3,100 $cm^{-1}$, or from 1,900 to 2,400 $cm^{-1}$.

12. The method for measuring a water concentration in ammonia as claimed in claim 1, wherein said measurement wave number is one or more selected from the group consisting of 3801, 3807, 3816, 3821, 3837 and 3854 $cm^{1}$ (variation width ±1 $cm^{-1}$).

* * * * *